(12) United States Patent
Chen et al.

(10) Patent No.: US 6,944,551 B2
(45) Date of Patent: Sep. 13, 2005

(54) IMAGING TRANSVERSE FLOW VELOCITY USING SPECTRAL BANDWIDTH OF THE DOPPLER FREQUENCY SHIFT IN PHASE-RESOLVED OPTICAL DOPPLER TOMOGRAPHY

(75) Inventors: Zhongping Chen, Irvine, CA (US); Hongwu Ren, Pasadena, CA (US); J. Stuart Nelson, Laguna Niguel, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/387,668

(22) Filed: Mar. 12, 2003

(65) Prior Publication Data

US 2003/0208326 A1 Nov. 6, 2003

Related U.S. Application Data

(60) Provisional application No. 60/363,580, filed on Mar. 12, 2002.

(51) Int. Cl.$^7$ ............................... G01F 1/00; G01F 7/00
(52) U.S. Cl. ....................................................... 702/49
(58) Field of Search ............................. 702/45, 49, 50, 702/66, 67, 159, 189, 190; 600/473, 476, 478, 479, 309, 310; 250/356.1, 356.01

(56) References Cited

U.S. PATENT DOCUMENTS

| | | | |
|---|---|---|---|
| 5,375,600 A | * 12/1994 | Melton et al. | ............... 600/455 |
| 5,991,697 A | 11/1999 | Nelson et al. | ................. 702/49 |
| 6,006,128 A | 12/1999 | Izatt et al. | ................... 600/476 |
| 6,325,762 B1 | * 12/2001 | Tjin | ........................... 600/505 |
| 6,549,801 B1 | * 4/2003 | Chen et al. | .................. 600/425 |

OTHER PUBLICATIONS

Wang et al., "Characterization of fluid flow velocity by optical Doppler tomography", Opt. Letter, 20:1337–1339, Jun. 1, 1995.*

Chen et al., "Optical Doppler tomographic imaging of fluid flow velocity in highly scattering media", Opt. Letter, 22:64–66, Jan. 1, 1997.*

* cited by examiner

Primary Examiner—Michael Nghiem
(74) Attorney, Agent, or Firm—Daniel L. Dawes; Myers Dawes Andras & Sherman LLP (57) ABSTRACT

The Doppler bandwidth extracted from the standard deviation of the frequency shift in phase-resolved optical Doppler tomography (ODT) is used to image the velocity component transverse to the probing beam. The effective numerical aperture (NA) of the optical objective determines the slope of the dependence of the standard deviation on velocity. In the case where the angle between the probing beam and flow direction is within ±15 degrees to the perpendicular, the Doppler frequency shift is very sensitive to angle position while the Doppler bandwidth is insensitive to flow direction. Linear dependence of the flow velocity on the Doppler bandwidth allows accurate measurement of flow velocity without precise determination of flow direction. In addition, it also extends the dynamic range of the average frequency shift mapping method used in the phase-resolved ODT.

13 Claims, 8 Drawing Sheets

| | | |
|---|---|---|
| 1 | 0.202 | 0.75 |
| 2 | 0.356 | 0.59 |
| 3 | 0.548 | 0.57 |
| 4 | 0.698 | 0.54 |
| 5 | 0.756 | 0.49 |
| 6 | 0.992 | 0.48 |
| 7 | 1.072 | 0.47 |
| 8 | 2.092 | 0.47 |

IMAGING TRANSVERSE FLOW VELOCITY USING SPECTRAL BANDWIDTH OF THE DOPPLER FREQUENCY SHIFT IN PHASE-RESOLVED OPTICAL DOPPLER TOMOGRAPHY

RELATED APPLICATIONS

The present application is related to U.S. Provisional Patent Application Ser. No. 60/363,580, filed on Mar. 12, 2002, which is incorporated herein by reference and to which priority is claimed pursuant to 35 USC 119.

GOVERNMENT SUPPORT

This invention was made with Government support under Grant No. HL84218 awarded by the National Institute of Health and under F49620-00-1-0371 awarded by the U.S. Air Force. The U.S. Government has certain rights in this invention.

BACKGROUND OF THE INVENTION

1. Field of the Invention

The invention relates to an improvement in imaging transverse flow velocities using spectral bandwidth of the Doppler frequency shift in phase-resolved optical Doppler tomography.

2. Description of the Prior Art

Optical Doppler tomography (ODT) combines Doppler velocimetry with optical coherence tomography (OCT) for noninvasive location and measurement of particle flow velocity in highly scattering media with micrometer-scale spatial resolution. The principle employed in ODT is very similar to that used in radar, sonar and medical ultrasound. ODT uses a low coherence source and optical interferometer to obtain high spatial resolution gating with a high speed scanning device such as a conventional rapid scanning optical delay line (RSOD) to perform fast ranging of microstructure and particle motion detection in biological tissues or other turbid media.

To detect the Doppler frequency shift signal induced by the moving particles, several algorithms and hardware schemes have been developed for ODT. The most straightforward method to determine the frequency shift involves the use of a small time fast Fourier transform (STFFT). However, the sensitivity of this method is mainly dependent on the FFT time window, which limits axial scanning speed and spatial resolution when measuring slowly moving blood flow in small vessels that requires high velocity sensitivity. However, a phase-resolved technique can decouple the Doppler sensitivity and spatial resolution while maintaining high axial scanning speed.

The limitation of phase-resolved ODT is that the dynamic range of the Doppler frequency shift measured is small because of an aliasing phenomenon caused by $2\pi$ ambiguity in the arctangent function. In Y. Zhao et. al., *Opt. Lett.* 25, 1358 (2000) on phase-resolved ODT, we reported on the use of the standard deviation of the Doppler spectrum to locate the microvasculature.

BRIEF SUMMARY OF THE INVENTION

The invention is an improvement in an optical Doppler interferometer such as described in Z. Chen, et. al. U.S. patent application Ser. No. 09/574,560 filed May 19, 2000 for "Phase-Resolved Optical Coherence Tomography and Optical Doppler Tomography for Imaging Fluid Flow in Tissue with Fast Scanning and High Velocity Sensitivity" issued as U.S. Pat. No. 6,549,801 (2003), which is incorporated herein by reference. The Doppler bandwidth extracted from the standard deviation of the frequency shift in phase-resolved functional optical coherence tomography (F-OCT) is used to image the velocity component transverse to the optical probing beam. It is found that above certain threshold level the Doppler bandwidth is a linear function of transverse flow velocity and the effective numerical aperture of the optical objective in the sample arm determines the slope of this dependence.

The Doppler bandwidth allows accurate measurement of flow velocity without the precise determination of flow direction when the Doppler flow angle is within ±15 degrees perpendicular to the probing beam. Such an approach extends the dynamic range of flow velocity measurements obtained using phase-resolved F-OCT.

More particularly the invention is defined as an improvement in a method for tomographic imaging of a fluid flow using phase-resolved functional optical coherence tomography (F-OCT) comprising the steps of extracting a Doppler bandwidth above a certain threshold level from the standard deviation of the frequency shift as a linear function of flow velocity by use of a optical probing beam, and imaging the flow velocity component transverse to the optical probing beam.

An interferometer with a sample arm having an optical objective with an effective numerical aperture is used to extract the Doppler bandwidth. The step of extracting the Doppler bandwidth as a linear function of flow velocity extracts the Doppler bandwidth as a linear function with a slope determined by the effective numerical aperture of the optical objective in the sample arm.

The optical probing beam extracts the Doppler bandwidth from the standard deviation and the step of extracting the Doppler bandwidth above a certain threshold level from the standard deviation of the frequency shift is performed without the precise determination of flow direction when the Doppler flow angle is within ±15 degrees perpendicular to the probing beam.

The step of extracting a Doppler bandwidth as a linear function of flow velocity is performed as defined by $$B_d = \frac{4V \sin\theta NA_{\mathit{eff}}}{\lambda}$$

where $B_d$ is the Doppler bandwidth, V is the flow velocity, $\lambda$ is the wavelength of the probing beam, $\theta$ is the Doppler angle and, $NA_{\mathit{eff}}$ is the effective numerical aperture and the Doppler bandwidth.

In the embodiment where the optical probing beam is a Gaussian beam, the standard deviation, $\sigma$, of the frequency shift is performed as defined by $$\sigma = \frac{\pi V \sin\theta NA_{\mathit{eff}}}{8\lambda}.$$

The standard deviation, $\sigma$, of the frequency shift is then performed as defined by $$\sigma = \frac{\pi V \sin\theta NA_{\mathit{eff}}}{8\lambda} + b$$

where b accounts for bandwidth spectrum broadening from contributions from Brownian motion and other factors that are independent of the macroscopic flow velocity.

The invention is further defined as an improvement in a method of using phase-resolved functional optical coherence tomography (F-OCT) comprising the steps of: measuring in an interferometer complex interference fringe signals $\Gamma_{ODT}(i,j)$ for each pixel; generating for each pixel a variance matrix $\sigma_{i,j}^2$ based on normalized variance values; generating an intensity map $I_{i,j}$ reflecting the axial distribution of backscattered intensities based on the amplitude, $A(T)$, obtained by using the complex fringe signals; averaging the $I_{i,j}$ over a predetermined set of scanning lines to obtain an axial intensity profile $I_i$; averaging temporally over the set, N, of axial scanning lines to find an axial variance profile $\sigma_i^2$, in which the variance values are weighted with respect to the intensity map $I_{i,j}$ $$\sigma_i^2 = \frac{\sum_{j=1}^{N} \sigma_{i,j}^2 I_{i,j}}{\sum_{j=1}^{N} I_{i,j}};$$

generating a normalized standard deviation profile $\sigma_i$ as an expression of the standard deviation of the Doppler power spectrum as a function of depth; and generating axial intensity profile $I_i$ to provide information on the backscattered intensity as a function of depth.

In another embodiment, the invention is an improvement in a method of using phase-resolved functional optical coherence tomography (F-OCT) comprising the steps of measuring in an interferometer complex interference fringe signals $\Gamma_{ODT}(i,j)$ for each pixel; generating for each pixel a variance matrix $\sigma_{i,j}^2$ based on normalized variance values; and generating an intensity map $I_{i,j}$ reflecting the axial distribution of backscattered intensities based on the amplitude, $A(T)$, obtained by using the complex fringe signals, where the generated tomographic intensity map $I_{i,j}$ and the standard deviation map $\sigma_{i,j}$ as maps of different particle sizes and different scattering parameters.

The invention also includes within its scope an apparatus for performing the foregoing improved methods. In this instance the optical apparatus used for performing the improved method is the same as or similar to that used in conventional phase-resolved functional optical coherence tomography (F-OCT), albeit combined with signal processing circuitry which performs the claimed data processing steps. Such signal processing circuitry includes analog or digital data processing circuits and in particular, all digital computers and/or digital signal processors of any type now known or later devised, which are capable of performing the claimed functions.

The present invention further includes the ability to measure a Doppler frequency shift proportional to a flow velocity component axial to the probing beam. Therefore, the flow direction can be determined from the flow velocity component axial to the probing beam and the flow velocity component transverse to the probing beam.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Figure 14:
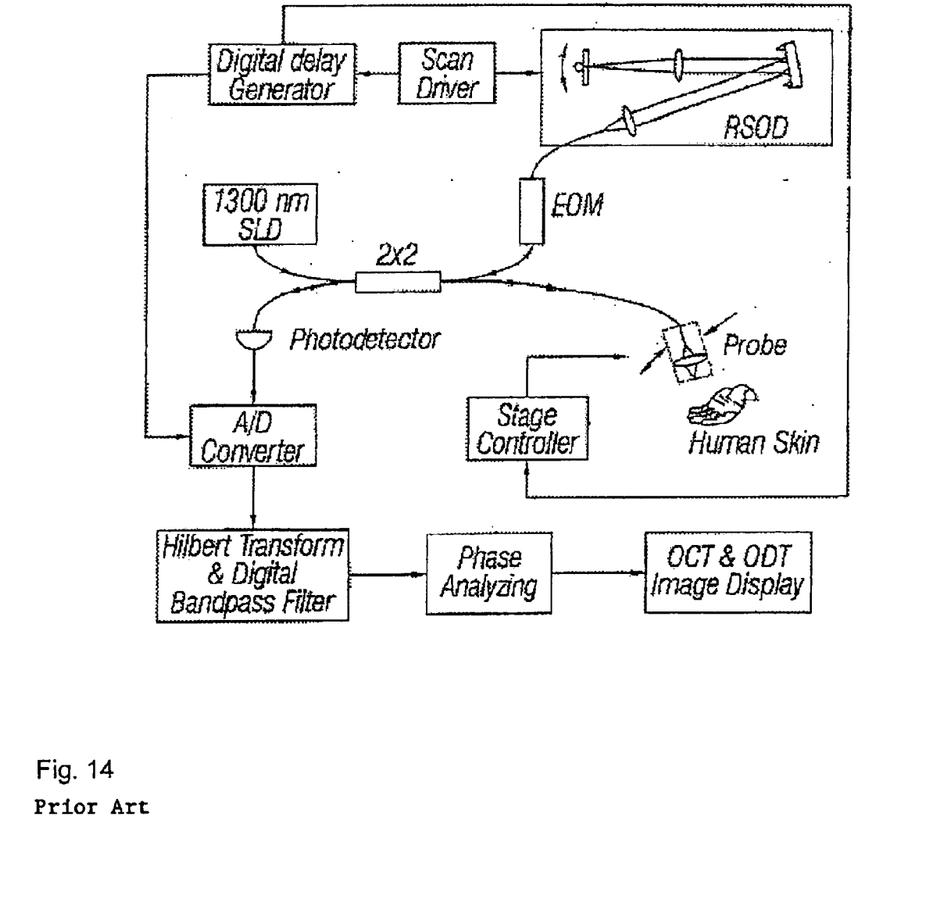
FIG. 14 is a symbolic block diagram of a functional optical coherence tomography system in which the method of the invention may be performed.

The standard deviation of the Doppler spectrum provides quantitative information on flow velocity. Using a simple geometric optics model, the linear dependence of the Doppler bandwidth on the flow velocity is theoretically derived and it is found that the effective numerical aperture (NA) of the optical objective in the sample arm in the functional optical coherence tomography system depicted in FIG. 14 and described in U.S. Pat. No. 6,549,801 determines the slope of this dependence. When flow velocity is much higher than that of the Brownian motion of the moving particle, the linear dependence of the flow velocity on the Doppler bandwidth allows accurate measurement of flow velocity transverse to the optical axis of the probing light beam.

Principle of Transverse Velocity Measurement

Phase-resolved ODT solves the compromise between spatial resolution and velocity sensitivity in the STFFT algorithm by mapping the phase change between sequential A-line signals for velocity detection. Phase-resolved ODT increases the imaging frame rate and it also increases the sensitivity of flow velocity detection by more than two orders of magnitude. The complex analytical function, $\tilde{\Gamma}_j(t)$, of each A-line ODT digitized fringe signal, $\Gamma_j(t)$, is calculated by the Hilbert transform $$\tilde{\Gamma}_j(t) = \Gamma_j(t) + iH\{\Gamma_j(t)\} = A(t)e^{i\psi(t)} \quad (1)$$

where H, A, $\psi$, j and t denotes the Hilbert transform, the amplitude and phase of the complex function $\tilde{\Gamma}_j(t)$, A-line number and RSOD group delay time, respectively. The average Doppler frequency shift and standard deviation of the Doppler spectrum for each pixel can be obtained simultaneously by the following equation, respectively, $$f_D(k) = \frac{1}{2\pi T}\tan^{-1}\left(\frac{\mathrm{Im}\left[\sum_{j=1}^{n}\tilde{\Gamma}_j(k)\cdot\tilde{\Gamma}_{j+1}^*(k)\right]}{\mathrm{Re}\left[\sum_{j=1}^{n}\tilde{\Gamma}_j(k)\cdot\tilde{\Gamma}_{j+1}^*(k)\right]}\right) \quad (2)$$

$$\sigma(k) = \sqrt{\frac{\int_{-\infty}^{+\infty}(f-f_D)^2 P(f)df}{\int_{-\infty}^{+\infty}P(f)df}} = \frac{1}{2\pi}\sqrt{\frac{2}{T^2}\left(1-\frac{\left|\sum_{j=1}^{n}\tilde{\Gamma}_j(k)\cdot\tilde{\Gamma}_{j+1}^*(k)\right|}{\sum_{j=1}^{n}\tilde{\Gamma}_j(k)\cdot\tilde{\Gamma}_j^*(k)}\right)} \quad (3)$$

where k is the pixel index, T is the A-line scanning period, Im denotes imaginary part and Re denotes real part of the complex value, f is the Doppler frequency shift, P(f) is Doppler power spectrum. From equation (2), the velocity limit known as $2\pi$ ambiguity velocity range is obtained as, $$V_{\max}^{f_d} = \frac{\lambda}{4\cos\theta}f_s \quad (4)$$

Equation (4) indicates that the maximum unambiguous velocity $V_{max}^{f_d}$ detected by the phase-resolved method is determined by the RSOD scanning speed $f_s$, the center wavelength of the optical source $\lambda$ and cosine of the Doppler angle $\theta$.

Figure 1:
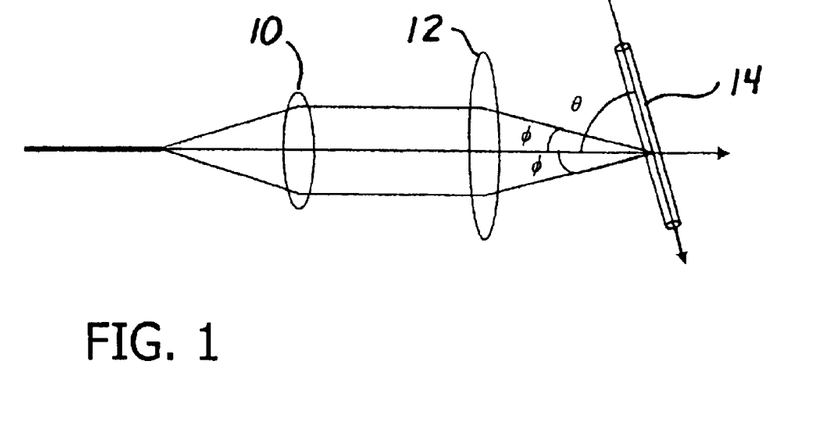
FIG. 1 is a diagram showing the probe beam geometry in the sample arm. θ is the Doppler angle between the optical axis and the flow velocity direction.

There are a number of factors that contribute to the broadening of the Doppler spectrum including Brownian motion, velocity gradient and turbulence and focusing beam geometry of the optical probing beam, which is not plane wave. When velocity is high, probing beam geometry dominates the broadening of the Doppler spectrum. The contribution from the focusing beam geometry can be derived from the optical geometry as show in FIG. 1. When the Doppler angle larger than $\tan^{-1}(2w/l_c)$, where w is waist radius of the optical Gaussian beam at the focus point and $l_c$ is the optical coherence length, the Doppler bandwidth is determined by the difference between two extreme average Doppler frequency shift caused by the two optical rays at the two boundaries of the probing optical beam. The average Doppler frequency shift corresponding to these two optical rays can be written as $$f_a = \frac{2V\cos(\theta-\phi)}{\lambda} \quad (5)$$

$$f_b = \frac{2V\cos(\theta+\phi)}{\lambda} \quad (6)$$

The estimated bandwidth of the Doppler signal derived from the above two equations is:

$$B_d = f_a - f_b = \frac{4V}{\lambda}\sin\phi\sin\theta = \frac{4V\sin\theta NA_{\mathit{eff}}}{\lambda} \quad (7)$$

In this equation, $B_d$ is the Doppler bandwidth, V is the flow velocity, $\phi$ is the optical aperture angle, $\theta$ is the Doppler angle and, $NA_{\mathit{eff}}$ is the effective numerical aperture. The Doppler bandwidth $B_d$ is defined by the above geometrical optics method.

For a Gaussian optical beam, the Doppler bandwidth $B_{1/e}$ (full width at 1/e of maximum spectrum amplitude) is the inverse of the transit time spent by particles passing through the focus zone of the Gaussian optical beam. The relationship between $B_{1/e}$ and $B_d$ is:

$$B_{1/e} = \frac{\pi}{8}B_d \quad (8)$$

Considering the relationship between the standard deviation and the Doppler bandwidth for a Gaussian optical beam, $$B_{1/e} = 4\sigma \quad (9)$$

the relationship between the standard deviation and $NA_{\mathit{eff}}$ can be derived as, $$\sigma = \frac{\pi V\sin\theta NA_{\mathit{eff}}}{8\lambda} \quad (10)$$

If we include the contributions from Brownian motion and other factors that are independent of the macroscopic flow velocity, equation (10) can be modified as, $$\sigma = \frac{\pi V\sin\theta NA_{\mathit{eff}}}{8\lambda} + b \quad (11)$$

where b accounts for bandwidth spectrum broadening from all of these sources. From the above theoretical result, the standard deviation is linearly dependent on velocity above a background value, and the effective numerical aperture $NA_{eff}$ of the optical objective in the sample arm determines the slope of this velocity dependence.

Knowing $NA_{eff}$, the measurement of the standard deviation can be used to determine the flow velocity. The flow velocity detected by the Doppler bandwidth method will be limited by the aliasing phenomenon being described by $\sigma \leq f_s$. However, because the Doppler bandwidth and standard deviation are much smaller than the average frequency shift in the flow conditions encountered in most cases, the Doppler bandwidth can extend the detection range of flow velocity. The range of velocity detection using the Doppler bandwidth method is determined by the following:

$$V_{max}^{\sigma} \sin\theta = \frac{8\lambda(f_s - b)}{\pi N A_{eff}} \qquad (12)$$

From equations (4) and (12), we can determine the ratio of the range of velocity detection for these two methods when they are directly applied with no phase unwrapping methods used, $$M = \frac{V_{max}^{\sigma}}{V_{max}^{f_d}} = \frac{32}{\pi N A_{eff} \tan\theta} \left(1 - \frac{b}{f_s}\right) \qquad (13)$$

The experimental system used for the Doppler bandwidth measurement is conventional and has been previously described in Y. Zhao et. al., *Opt Left.* 25, 114 (2000); and Y. Zhao et. al., *Opt. Lett.* 25, 1358 (2000). The optical source for the fiber interferometer is a low coherence ASE broadband source, whose output power, center wavelength, and bandwidth is 5 mW, 1300 nm and 65 nm, respectively. The source is coupled to the source arm and split into reference and sample arms by a 3-dB 2×2 coupler. A rapid-scanning optical delay line (RSOD) in a group delay scanning mode is used for 500 Hz A-line scanning, and an E-O phase modulator at 500 kHz with a ramp signal is used as a carrier frequency producer to implement a heterodyne detection scheme.

In the sample arm shown in FIG. 1, an exchangeable optical collimator 10 and an optical objective 12 (20×, N.A., 0.35) are used to focus the optical beam to the center of a capillary tube whose inner diameter is 900 $\mu$m for M-mode imaging. A 0.1% intralipid solution composed of particles (0.356 micrometer diameter) is used as the turbid media, and a syringe pump driven by a high-resolution translation stage controls its flow through the capillary tube 14. In the detection arm, the signal from the photodetector is amplified with a bandpass preamplifier and then sent to an analog-to-digital conversion and data acquisition board sampling at 5 MHz, the number of data points for each A-line data acquisition is 4096. The A-line scanning of RSOD, phase modulation of the E-O phase modulator and data acquisition of the data acquisition board are synchronized in order to get precise alignment of the original phase of the sequential A-line scans.

Results and Analysis

Figure 2:
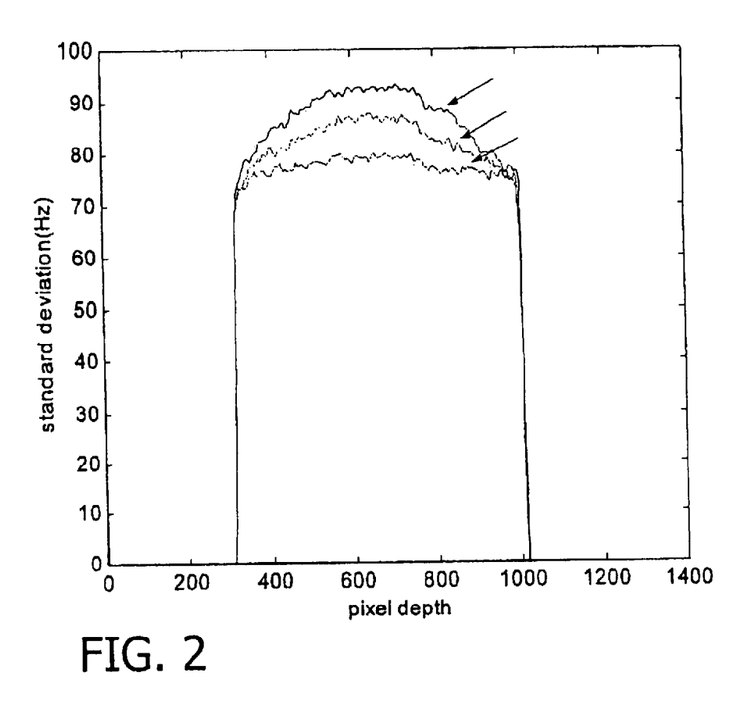
FIG. 2 is a graph showing the standard deviation flow profile in the center of the capillary.
Figure 3:
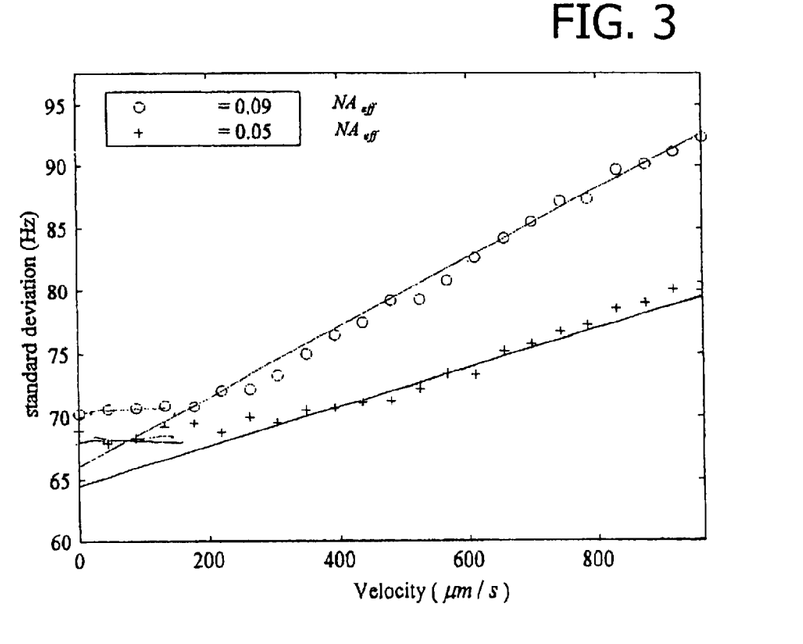
FIG. 3 is a graph of the standard deviation dependence on velocity and $NA_{eff}$ at Doppler angle 77 degree°, the solid line is theoretical curve from equation (11). For $NA_{eff}$ equals 0.09 and 0.05, the background b is 66 and 64.5 Hz, respectively.
Figure 4:
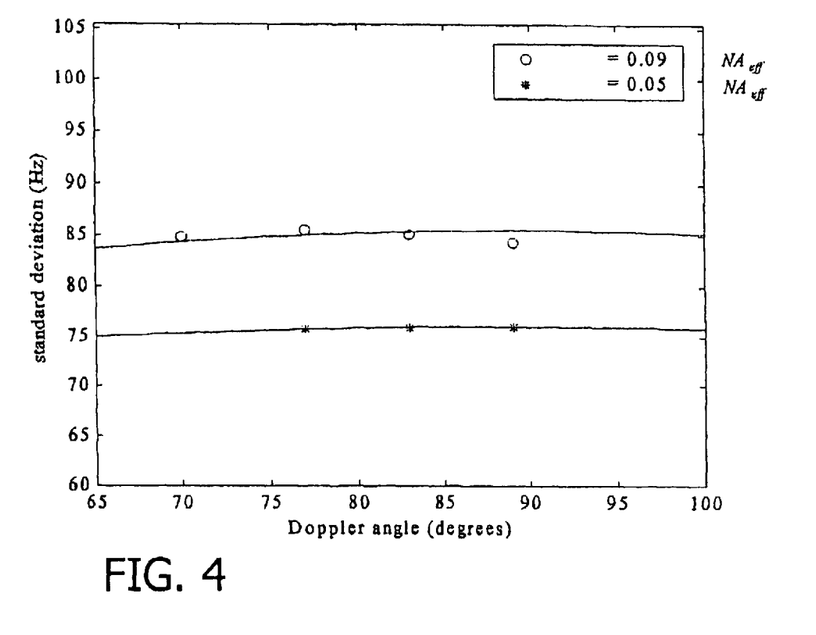
FIG. 4 is a graph of the standard deviation at different Doppler flow angles for two $NA_{eff}$ 0.09 and 0.05 when the flow velocity is 698 µm/s. The background b when the effective NA equals 0.09 and 0.05 is 65.6 and 64.8 Hz, respectively.
Figure 5:
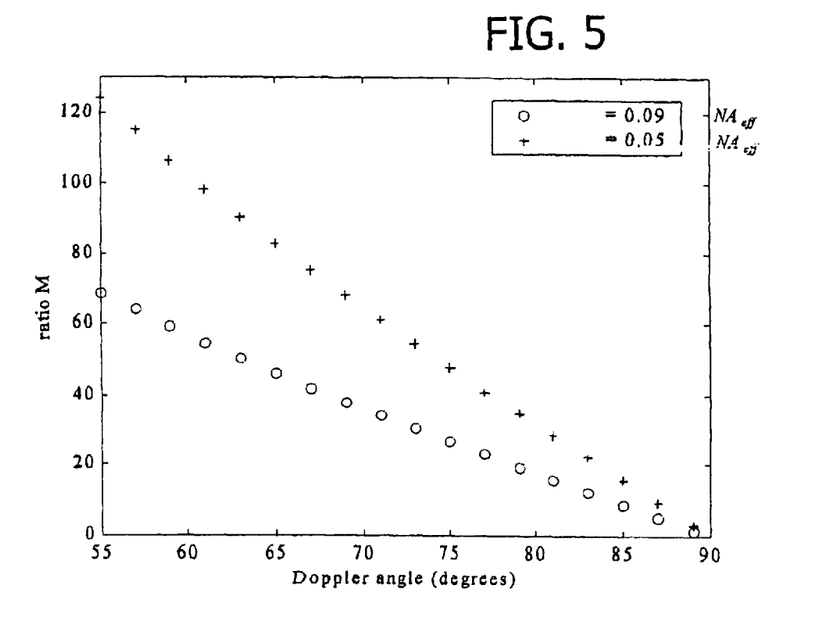
FIG. 5 is a graph of the ratio of the detection range of velocity by the Doppler bandwidth and average frequency shift mapping methods. The scanning frequency rate of the RSOD is 500 Hz, and the background of standard deviation b is 70 Hz, which corresponds to the value determined in our experiment.

The standard deviation images of the intralipid flow in the center section of the capillary tube for different $NA_{eff}$, Doppler flow angle $\theta$ are captured for a velocity from 0 to 960 $\mu$m/s. The position of the focus point of the optical probing beam is fixed to the center of the tube 14. The profiles of the flow standard deviation images for three velocities are shown in FIG. 2. We extract the center part of every flow standard deviation profile for a velocity from 0 to 960 $\mu$m/s to study the relationship between Doppler bandwidth and velocity. The extracted result from the center part of every standard deviation profile corresponds to the top of the parabolic flow profile in the tube. The experimental standard deviation data and theoretical curves from equation (11) are shown in FIG. 3 when $NA_{eff}$ equals 0.09 and 0.05 at Doppler angle 77°. The solid and dotted lines are the theoretical curves and experiment results respectively. The theoretical and experimental curves are in good agreement for velocities higher than 300 $\mu$m/s. For $NA_{eff}$ equals 0.09 and 0.05, the background b is 66 and 64.5 Hz, respectively. At low flow velocity, the standard deviation is constant. This is because at low velocity Brownian motion, which is independent of the macroscopic flow velocity, dominates the Doppler bandwidth. The regime for velocities higher than 300 $\mu$m/s is dominated by Doppler bandwidth broadening originated from the optical beam geometry. FIG. 3 indicates that the slope of the Doppler bandwidth dependence on velocity is proportional to $NA_{eff}$. The standard deviation experimental data and theoretical calculations for different angles and two $NA_{eff}$ values 0.09 and 0.05 at a velocity of 698 $\mu$m/s are shown in FIG. 4. FIG. 4 indicates that the dependence of Doppler bandwidth is insensitive to Doppler angles around 90°. The background b when the effective NA equals 0.09 and 0.05 is 65.6 and 64.8 Hz, respectively. Therefore the Doppler bandwidth component in the standard deviation can be used in this situation to measure transverse velocity. It can be used in intravascular imaging blood flow using endoscopic optical coherence tomography where the Doppler angle is around 90°, and most of the blood vessels are parallel to the surface of the skin, so this method has its merit for this reason. From FIG. 3, it was determined that there is no aliasing phenomenon even though the velocity has reached 960 $\mu$m/s, which is much higher than the largest measurable velocity with the average Doppler frequency shift mapping method described by equation (4). This is because the standard deviation is only a small fraction of the average Doppler frequency shift as explained by equation (13). The ratio M theoretical curves are plotted in FIG. 5 for two different $NA_{eff}$. FIG. 5 indicates that the unambiguous detection range of velocities using the Doppler bandwidth mapping method can be many (10~20) times larger than the corresponding average Doppler frequency shift mapping method when the Doppler angle is in the range from 70° to 85°. Therefore the Doppler bandwidth mapping method is a promising tool for overcoming the $2\pi$ ambiguity of velocity detection in the average Doppler frequency shift mapping method.

The Doppler bandwidth can be used to measure flow velocity transverse to the probing beam direction. Using a geometric optics model, the linear dependence of the Doppler bandwidth on flow velocity is theoretically derived and it is found that the slope of this dependence is determined by the $NA_{eff}$ of the optical objective. Above a certain threshold flow velocity, this linear relationship is in good agreement with experimental data. In the case where the angle between the probing optical beam and flow direction is within ±15 degrees to the perpendicular, the average Doppler frequency shift is very sensitive to angle position while the Doppler bandwidth is insensitive to flow direction. Linear dependence of the flow velocity on the Doppler bandwidth allows accurate measurement of flow velocity without precise determination of flow direction. Finally, this technique also extends the dynamic range of the average Doppler frequency shift mapping method used in the phase-resolved ODT.

Figure 6:
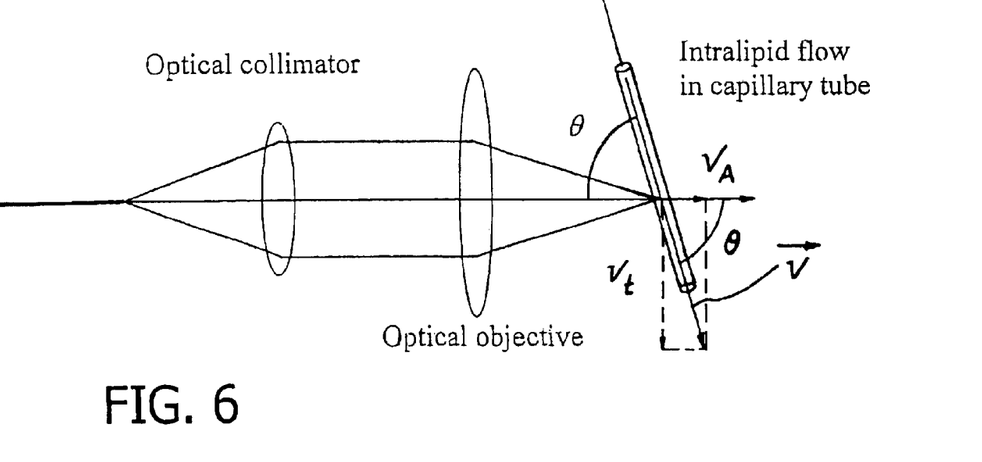
FIG. 6 is a graphical representation showing that flow velocity magnitude and direction is determined based on the calculated flow velocity transverse to the probing beam $V_1$ and the calculated flow velocity axial to the probing beam $V_A$.

Now referring to FIG. 6, the magnitude and direction of flow velocity vector $\overline{V}$ is determined. As set forth above, the velocity transverse to the probing beam direction $V_\perp$, is proportional to the Doppler bandwidth. Also, the velocity axial to the probing beam direction $V_A$ is proportional to the Doppler frequency shift. Therefore, velocity $\vec{V}$ is determined, as shown, as well as the angle $\theta$ between probing optical beam and the flow direction.

Light Scattering in the Single and the Multiple Scattering Regimes

From known light scattering theory, the expected spectrum obtained from a monodisperse dilute suspension undergoing Browninan Motion has a Lorentzian shape. In the following analysis, we will differentiate between the single and the multiple scattering regimes.

In the single scattering regime, we apply the dynamic light scattering theory (DLS). Assuming weak scattering as well as non-interacting particles, the linewidth $\Omega$ of the power Doppler spectrum (in this case defined as the half width at half maximum) is proportional to the particle self-diffusion coefficient $D_B$ as follows:

$$\Omega = q^2 D_B; \quad D_B = \frac{k_B T}{3\pi\eta a} \quad (14)$$

where $k_B$ is the Boltzman constant, T is the temperature, $\eta$ is the viscosity of the suspending liquid and $\alpha$ is the hydrodynamic diameter of the scattering particle. Further, q denotes the photon momentum transfer, $$q = 2k\sin\frac{\theta}{2},$$

where k is the wave vector in the scattering medium and $\theta$ is the scattering angle.

In an optical dense medium where light scatters multiple times before detection, the scattering angle, the polarization of the scattered wave, and consequently the momentum transfer q change with each scattering event. In order to describe this situation, we need to apply the theory of diffusing wave spectroscopy (DWS). When considering light diffusion through a medium where light scatters multiple times, the power Doppler spectrum is still a Lorentzian, but the linewidth $\Omega$ will be dependent upon the scattering properties of the medium and the photon pathlength within it.

$$\Omega = 2k^2 D_B \frac{s}{l^*}; \quad D_B = \frac{k_B T}{3\pi\eta a} \quad (15)$$

where s is the pathlength traveled by the light in the medium, $l^* = l_s/(1-g)$ is the photon random walk length, $l_s = 1/\mu_s$ is the photon scattering length, and g is the scattering anisotropy of the medium (defined as an average of the cosine of the scattering angle).

Standard Deviation Mapping of Dynamic Particle Properties

The linewidth $\Omega$ is related to the standard deviation/variance of the power Doppler spectrum. The ODT variance imaging technique offers a means for mapping the variance of the power Doppler spectrum with high scanning rates and high spatial resolution. The variance imaging technique is used to map particle dynamics.

Figure 7:
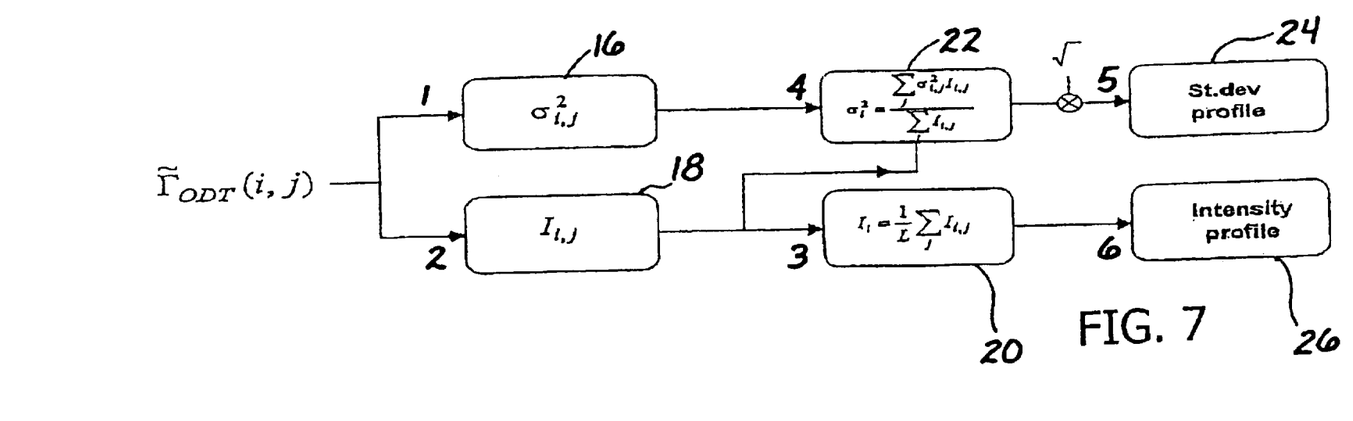
FIG. 7 is a block diagram illustrating the steps used in acquisition of variance and intensity profiles.

The probe configuration is illustrated in FIG. 7. The scanning parameters are listed in Table 1. A 1310 nm OCT/ODT system includes a 1310 nm SLD source with 10.2 mW output power and a heterodyne detection technique which gives a dynamic range of 120 dB. Applying confocal optics with low NA, and thus a large confocal parameter makes it possible to perform axial scans using a static focus. This gives the possibility for higher scan rates compared to what is the case when using dynamic focusing. Both the confocal configuration of the probe and the coherence gate effectively discriminates multiple scattered light. Adequate measurements can thus be obtained even, when the axial scanning range exceeds the length of the confocal parameter. However, we can not, assume that the lateral resolution is constant all over the scanning range, which was set to 900 $\mu$m.

TABLE 1

| Parameter | Symbol | Value | Unit |
|---|---|---|---|
| Source bandwidth | $\Delta\lambda$ | 80 | nm |
| Center frequency of the source | $\lambda_0$ | 1310 | nm |
| Coherence length | $l_c$ | 10 | $\mu$m |
| Confocal parameter | b | 120 | $\mu$m |
| Source power | P | 10.2 | mW |
| Lateral resolution | $\Delta x$ | 10 | $\mu$m |
| Modulation frequency | $f_{mod}$ | 500 | kHz |
| Numerical aperture | NA | 0.13 | — |
| Sampling rate | $f_{samp}$ | 5 | MHz |
| Scan rate | $f_s$ | 500 | Hz |

The measurements are extremely sensitive to environmental vibrations. As a consequence, all measurements were done on an optical table with laminar air flow isolation (Newport Corporation, Irvine Calif.).

In the experiments we applied eight different homogeneous suspensions containing monodisperse polystyrene microsphere particles (Polysciences, Inc., Warrington Penn.), with diameters ranging From 0.2 to 2.0 $\mu$m. The suspensions were kept at room temperature T=294 K for a certain time to assure equal temperature in all the suspensions before starting the measurements. The temperature was also measured after data acquisition. In some of the experiments, we wanted to immobilize the polystyrene particles in a gel before doing measurements. For this purpose the particle suspensions were mixed in a 50:50 volume ratio with a 4% gelatin suspension.

During data acquisition, a fixed position of the focus was used, both axially arid laterally. The scanning frequency was $f_s$=500 Hz. The focus spot was placed right below the end of the axial scanning range. A schematic overview of the post processing technique used to obtain the data is given in FIG. 7. In step 16 a variance matrix $\sigma_{i,j}^2$ is calculated based on the complex interference fringe signals $\Gamma_{ODT}(i,j)$. In total, n=4000 sequential axial scans are performed, and 200 sequential axial scans are used to build up each axial scan line, thus j∈[1,n/200]. The variance matrix $\sigma_{i,j}^2$ contains the normalized variance values.

In step 18 an intensity map $I_{i,j}$ is calculated, reflecting the axial distribution of backscattered intensities. The intensity values are based on the amplitude $A(\tau)$, obtained by using the complex fringe signals. As in step 16, 200 axial scans were used to construct each intensity line.

In step 20 the intensity is averaged over n/200 scanning lines, to obtain an axial intensity profile $I_i$. This is equivalent to performing temporal averaging.

In step 22 when averaging temporally over n/200 axial scanning lines to find an axial variance profile $\sigma_i^2$, the variance values are weighted with respect to the intensity map $I_{i,j}$ $$\sigma_i^2 = \frac{\sum_{j=1}^{n/200} \sigma_{i,j}^2 I_{i,j}}{\sum_{j=1}^{n/200} I_{i,j}}$$

By weighting the variance with respect to the intensity, we assure that the points with the largest signal-to-noise ratio (SNR) ratio contribute most to the results. The signal-to-noise ratio is a crucial factor, which will have influence on the broadness of the Doppler spectrum.

In step 24 the normalized standard deviation profile $\sigma_i$ expresses the standard deviation of the Doppler power spectrum as a function of depth, and may identify the transition region between the single and the multiple scattering regimes.

In step 26 the axial intensity profile $I_i$ provides information on the backscattered intensity as a function of depth in the suspension. It is an important tool for identifying the spatial extent of the single scattering regime.

Figure 8:
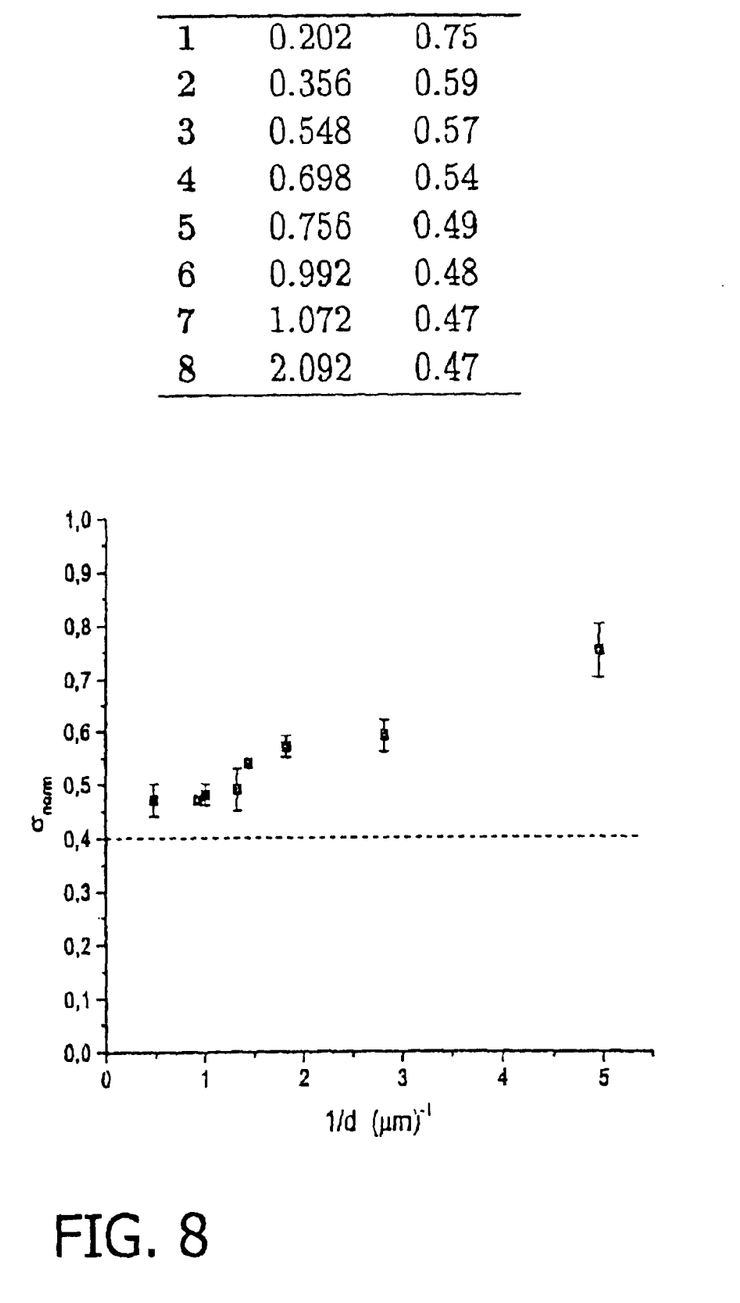
FIG. 8 is a graph of the normalized standard deviation $\sigma_{norm}$ of the Doppler spectrum as a function of inverse particle diameter. Intervals show the statistical uncertainty of the standard deviation measurements after five repetitions. The horizontal dotted line shows the intrinsic value of the standard deviation, obtained by immobilizing the scatterers in a gelatin gel. This intrinsic value is believed to originate from the background noise. The values tabulated are the normalized standard deviation values in a single scattering regime, found by averaging the axial standard deviation profile in the range 0 to 30 µm below the liquid surface.

FIG. 8 lists the normalized standard deviation of the Doppler spectrum in the single scattering regime, measured in polystyrene suspensions. These values are obtained by spatial averaging of the axial standard deviation profile over the range from 0 to 30 μm below the liquid surface. This corresponds to an optical depth less than one scattering length ($1/\mu_s$) for all suspensions, except for the suspension with d=2.092 μm. FIG. 8 also shows a graphical presentation of the results.

We are interested in the value of the normalized standard deviation obtained in the absence of Brownian motion. This value was experimentally determined by mixing the polystyrene suspensions with d=0.356 μm and d=0.548 μm with a 4% gelatin suspension. In such a mixture, the viscosity factor η in equation (14) and (15) comes close to infinity, and thus the effects originating from particle movement can be neglected. The horizontal line in FIG. 8 illustrates the intrinsic value of the standard deviation, found to have the value 0.4.

Power Spectra in the Single Scattering Regime

To demonstrate that fast scanning optical Doppler tomography systems can be used to image and quantify Brownian Motion within highly scattering media, we determined the power Doppler spectra for separate monodisperse suspension of polystyrene microspheres. The measurements were done in the single scattering regime, and the linewidth Ω of the spectra was used to estimate an experimental Brownian diffusion coefficient $\hat{D}_B$ for each sample.

Recording and Processing of Data

The data was obtained by using an ODT technique with conventional post processing, with no lateral or axial movement of the focus during data acquisition. The focus spot was placed 20 μm below the liquid surface. The data was acquired using 4000 sequential axial scans, which corresponds to a total acquisition time of 8 seconds at a scanning frequency of 500 Hz.

Figure 9:
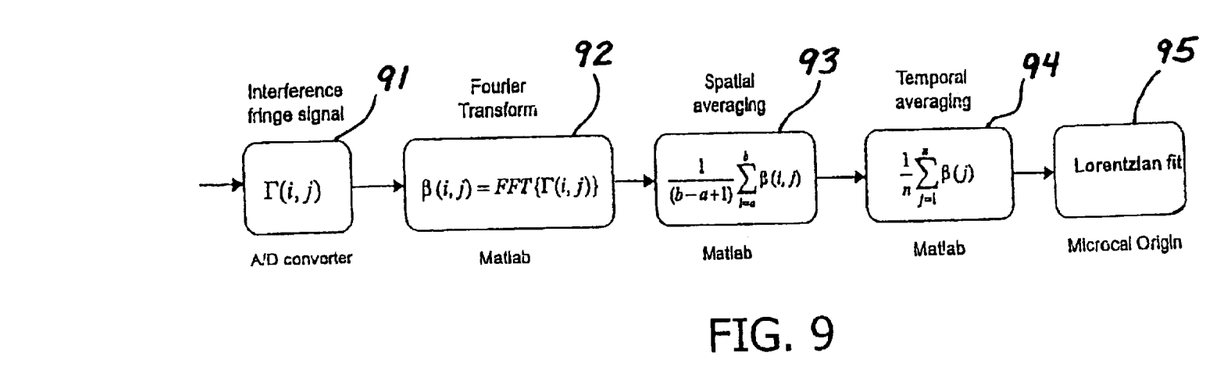
FIG. 9 is a schematic block diagram of the processing technique used to perform a Lorentzian fit corresponding to the measured discrete power Doppler spectra for a range of particle sizes.

For each sample, we apply a post processing technique as illustrated in FIG. 9. Sequential steps 91 through 95 are shown. This made it possible to perform a Lorentzian fit to the measured discrete power Doppler spectra for various particle sizes. Knowing the Lorentzian approximation of the power Doppler spectrum, the linewidth Ω as a function of particle size in the single scattering regime, could be obtained.

Referring to step 91, the raw data of the interference fringe was obtained using a 12 bit A/D converter with a sampling frequency of 5 MHz. The real valued interference fringe functions $\Gamma_{ODT}(T_i)$ were received and stored in a personal computer, using software developed at Beckman Laser Institute (Irvine, Calif.).

As described, the focus was fixed during data acquisition, and the interference fringe data can be described by the two dimensional matrix $\Gamma(i,j)$, where i denotes the axial coordinate defined by the coherence gate, and j denotes the scan number, i∈[0,900], j∈[1, n]; n=4000.

Referring to step 92, the matrix $\Gamma(i,j)$ was exported to MATLAB, where the FFT of $\Gamma(i,j)$ was calculated. We thus obtained a two-dimensional matrix containing discrete power Doppler spectra, described by $\beta(i,j)$.

Referring to steps 93 and 94, power Doppler spectra in each axial scanning line j ranging in depth from 20 to 37 μm below the liquid surface were averaged (spatial averaging corresponding to the pixel range a≦i≦b). Using selected scattering parameters, we conclude that this depth interval theoretically lies within the single scattering regime. Thereafter, for the selected depth range, we averaged the power Doppler spectrum over 4000 subsequent axial-lines (temporal averaging).

Referring to step 95, the discrete power Doppler spectrum obtained after performing FFT and averaging were exported to Microcal Origin (Microsoft) where a Lorentzian curve fit was performed. In order to mathematically being able to able to perform the Lorentzian fits to the power Doppler spectra, a power offset value has to be introduced. This is due to the background noise.

The linewidth Ω need from this Lorentzian fit, was used to determine $\hat{D}_B$, the experimental Brownian diffusion coefficient. $\hat{D}_B$ was compared with the theoretical values, given by equation (15) with the results summarized below.

Results

Figure 10:
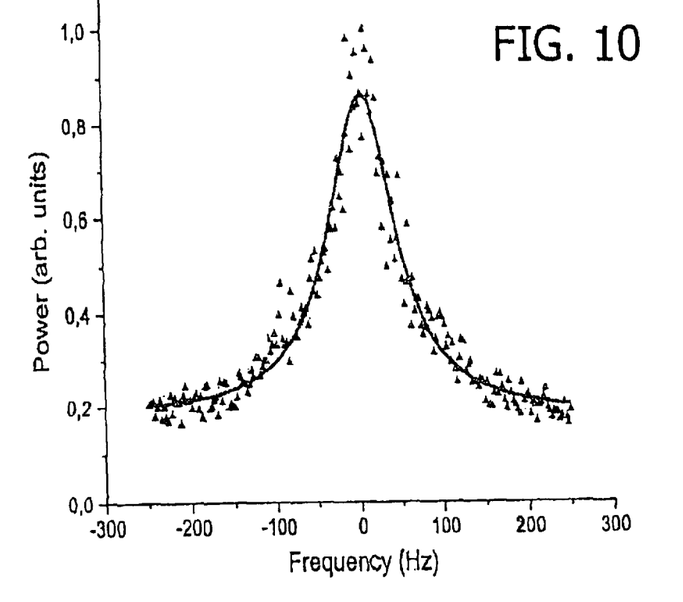
FIG. 10 is a graph showing the normalized power Doppler spectrum for particle size d=0.356 µm and corresponding Lorentzian fit.

FIG. 10 shows the discrete power Doppler spectrum and the Lorentzian fit for the mono disperse suspension containing the particle size d=0.356 μm.

Figure 11:
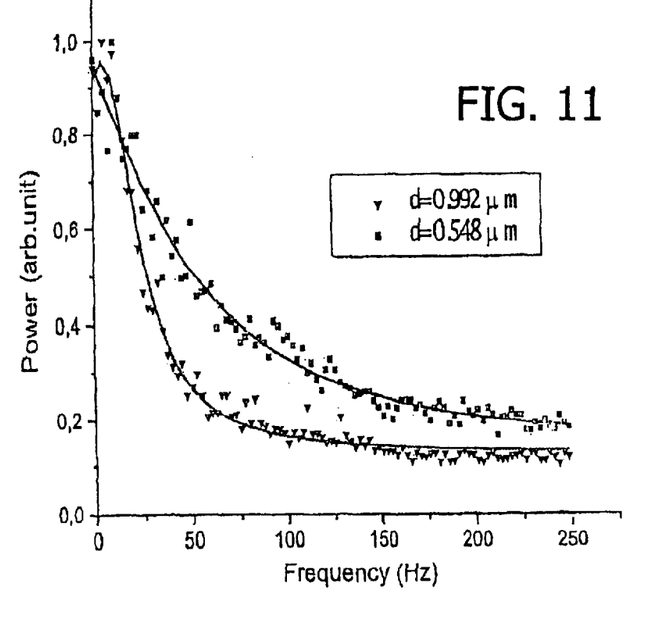
FIG. 11 is a graph of the right half of normalized power Doppler spectra for the particle sizes d=0.548 µm and d=0.992 µm and corresponding Lorentzian fits.

FIG. 11 shows the right half of the discrete power Doppler spectra obtained for the polystyrene particles with diameters d=0.548 μm and d=0.992 μm. Lorentzian fits are inserted. The intention is to visualize the change in linewidth Ω of power Doppler spectra for different polystyrene suspensions. For this purpose, showing the right half of the spectrum is sufficient.

Figure 12:
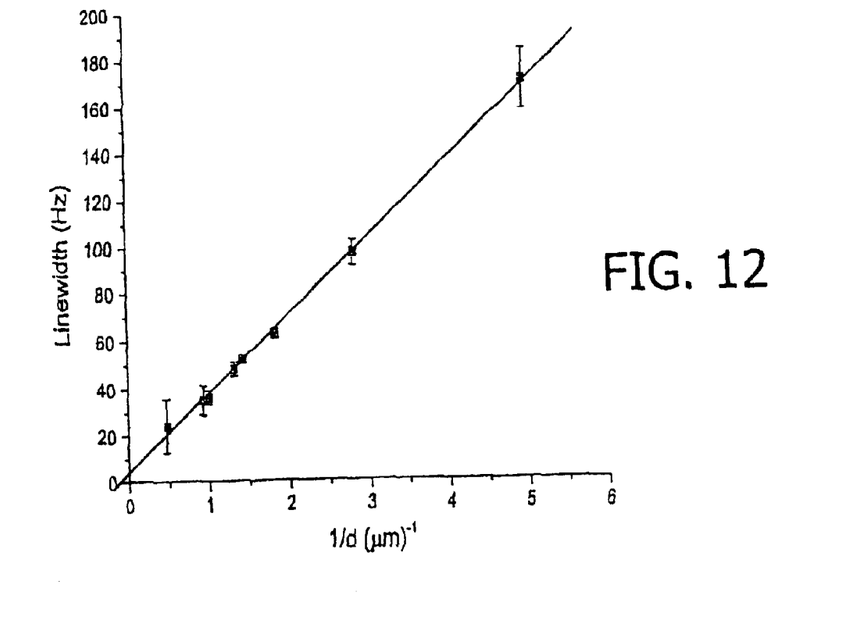
FIG. 12 is a graph of the measure linewidth Ω as a function of inverse diameter particle size for five independent measurements.

FIG. 12 illustrates the resulting relationship between the inverse particle size and the measured linewidth Ω. Error bars show the standard deviation in linewidth Ω, measured from the Lorentzian fits for 5 independent measurements. The solid line indicates a linear regression fit to the data points.

One problem that arises when measuring the power Doppler spectrum, is the background signal originating from the EOM. The effect can be observed in FIG. 10. Notice the data points with higher power values than what should be expected for frequencies around f=0 Hz.

Further, from FIG. 12 we can conclude that the statistical uncertainty in the estimate of Ω is largest for d=2.092 μm and d=0.202 μm. For d=0.202 μm, which yields Ω=171 Hz, the linewidth Ω is relatively close to the maximum detectable linewidth of 250 Hz, defined by the Nyquist sampling theorem. For d=2.092 μm, and Ω=24 Hz, the small linewidth complicates the process of fitting the Lorentzian curve to the discrete power Doppler spectrum.

As can be observed in FIG. 10, a Lorentzian curve approximates the acquired power Doppler spectra in the single scattering regime. As further shown in FIGS. 11 and 12, the linewidth Ω appears to be proportional to the inverse of the particle diameter, which is in accordance with equation (14).

Using equation (14), an experimental value of the Brownian diffusion coefficient, $\hat{D}_B$, could be calculated based on the measured linewidths $\Omega$. Neglecting the measurement for the largest particles size, due to the difficulties performing the Lorentzian fit, the accuracy of $\hat{D}_B$ compared to the theoretical value was better than 7.5%.

Power Spectra in the Multiple Scattering

Using the experimental setup described herein, the linewidth $\Omega$ of the power Doppler spectra may be studied as a function of depth in the polystyrene suspension. This is analogous to prior experiments where broadening of the spectrum with increasing depth was observed. This was interpreted as being caused by multiple scattering of the detected photons.

According to equation (15) the linewidth $\Omega$ in the multiple scattering regime should increase linearly with path length s traveled by the light in the medium. This is experimentally verified as described herein.

Recording and Processing of the Data

The focus spot was placed right below the end of the axial scanning range. Since the axial scanning range was 900 $\mu$m, we needed a suspension with a relatively short scattering length $l=1/\mu_s$ in order to detect photons originating from the multiple scattering regime. The polystyrene suspension with particle diameter d=0.548 $\mu$m with a scattering; length of 93 $\mu$m was selected.

The acquisition technique and the postprocessing methods are equivalent to the ones described above. However, in this case we selected non-overlapping depth intervals, [a,b], distributed all over the total scanning range. Power Doppler spectra for several depths could thus be obtained.

Figure 13:
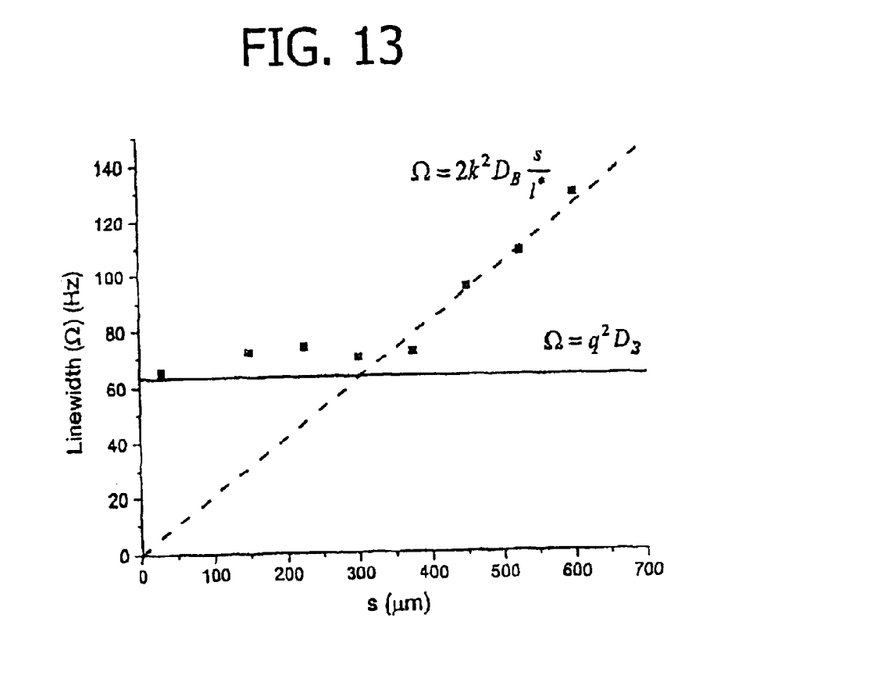
FIG. 13 is a graph of linewidth Ω as a function of photon path length s in the suspension of polystyrene particles with diameter d=0.548 µm.

The results are illustrated in FIG. 13 where the measured linewidth $\Omega$ as a function of the pathlength s traveled by the light in the suspension of polystyrene particles with diameter d=0.548 $\mu$m. The horizontal solid line shows the approximation found in the single scattering regime. The broken line shows the approximation found for the multiple scattering regime, obtained by using equation (15).

As we detect photons having longer pathlengths s, the linewidth of the power Doppler spectrum increases rapidly. As s increases, according to the Nyquist limit, aliasing may represent a problem when using a scanning frequency $f_s$ of 500 Hz. Constructing a scanning mechanism capable of increasing $f_s$ may represent a solution.

Furthermore, the signal power decreases exponentially with depth, and as we detect power spectra deeper in the suspension, the poor signal-to-noise ratio (SNR) complicates the process of performing the Lorentzian fits.

The estimated value of $\hat{D}_B$ in the multiple scattering regime, given in table 3.4, is approximately 2.3 times smaller than expected. The fast scanning OCT system used in our experiment seems not capable of resolving particle dynamics in the multiple scattering regime. Increasing $f_s$ and SNR may improve our experimental results.

FIG. 13 indicates that for a photon pathlength in the sample between 300 $\mu$m and 400 $\mu$m, we observe that the linewidth starts to increase almost linearly. This is an indication identification of the transition region between the two scattering regimes may be possible.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

What is claimed is:

1. An improvement in a method for tomographic imaging of a fluid flow using phase-resolved functional optical coherence tomography (F-OCT) comprising:
    extracting a Doppler bandwidth above a certain threshold level from the standard deviation of the frequency shift as a linear function of flow velocity by use of an optical probing beam; and
    imaging the flow velocity component transverse to the optical probing beam.

2. The improvement of claim 1 where an interferometer with a sample arm having an optical objective with a effective numerical aperture is used to extract the Doppler bandwidth, and where extracting the Doppler bandwidth as a linear function of flow velocity extracts the Doppler bandwidth as a linear function with a slope determined by the effective numerical aperture of the optical objective in the sample arm.

3. The improvement of claim 1 where the optical probing beam extracts the Doppler bandwidth from the standard deviation and where extracting the Doppler bandwidth above a certain threshold level from the standard deviation of the frequency shift is performed without the precise determination of flow direction when the Doppler flow angle is within ±15 degrees perpendicular to the probing beam.

4. The improvement of claim 1 where extracting a Doppler bandwidth as a linear function of flow velocity is performed as defined by $$B_d = \frac{4V\sin\theta NA_{e\!f\!f}}{\lambda}$$

where $B_d$ is the Doppler bandwidth, V is the flow velocity, $\lambda$ is the wavelength of the probing beam, $\theta$ is the Doppler angle and, $NA_{e\!f\!f}$ is the effective numerical aperture and the Doppler bandwidth.

5. The improvement of claim 4 where the optical probing beam is a Gaussian beam and where the standard deviation, $\sigma$, of the frequency shift is performed as defined by $$\sigma = \frac{\pi V \sin\theta NA_{e\!f\!f}}{8\lambda}.$$

6. The improvement of claim 5 where the standard deviation, $\sigma$, of the frequency shift is performed as defined by $$\sigma = \frac{\pi V \sin\theta NA_{e\!f\!f}}{8\lambda} + b$$

where b accounts for bandwidth spectrum broadening from contributions from Brownian motion and other factors that are independent of the macroscopic flow velocity.

7. The improvement of claim 1, further comprising:
measuring a Doppler frequency shift proportional to a flow velocity component axial to the probing beam; and
determining a flow direction from the flow velocity component axial to the probing beam and the flow velocity component transverse to the probing beam.

8. An improvement in an apparatus for tomographic imaging of a fluid flow using phase-resolved functional optical coherence tomography (F-OCT) comprising:
means for extracting a Doppler bandwidth above a certain threshold level from the standard deviation of the frequency shift as a linear function of flow velocity by use of an optical probing beam; and
means for imaging the flow velocity component transverse to the optical probing beam.

9. The improvement of claim 8 where the means for extracting comprises an interferometer with a sample arm having an optical objective with a effective numerical aperture is used to extract the Doppler bandwidth, and where the means for extracting the Doppler bandwidth as a linear function of flow velocity extracts the Doppler bandwidth as a linear function with a slope determined by the effective numerical aperture of the optical objective in the sample arm.

10. The improvement of claim 8 where the means for extracting comprises an optical probing beam and where the means for extracting the Doppler bandwidth above a certain threshold level from the standard deviation of the frequency shift performs without the precise determination of flow direction when the Doppler flow angle is within ±15 degrees perpendicular to the probing beam.

11. The improvement of claim 10 where the optical probing beam is a Gaussian beam and where means for extracting generates a standard deviation, $\sigma$, of the frequency shift is performed as defined by $$\sigma = \frac{\pi V \sin\theta NA_{e\!f\!f}}{8\lambda}.$$

12. The improvement of claim 11 where the means for generating the standard deviation, $\sigma$, of the frequency shift performs as defined by $$\sigma = \frac{\pi V \sin\theta NA_{e\!f\!f}}{8\lambda} + b$$

where b accounts for bandwidth spectrum broadening from contributions from Brownian motion and other factors that are independent of the macroscopic flow velocity.

13. The improvement of claim 8 where the means for extracting a Doppler bandwidth as a linear function of flow velocity performs as defined by $$B_d = \frac{4V\sin\theta NA_{e\!f\!f}}{\lambda}$$

where $B_d$ is the Doppler bandwidth, V is the flow velocity, $\lambda$ is the wavelength of the probing beam, $\theta$ is the Doppler angle and, $NA_{e\!f\!f}$ is the effective numerical aperture and the Doppler bandwidth.

* * * * *